(12) United States Patent
Markov et al.

(10) Patent No.: US 8,186,515 B2
(45) Date of Patent: May 29, 2012

(54) METHOD AND SEPARATOR SYSTEM FOR SEPARATING MAGNETIC PARTICLES, SEPARATOR COLUMN FOR USE IN A SEPARATOR SYSTEM

(75) Inventors: Denis Markov, Veldhoven (NL); Hans Marc Bert Boeve, Hechtel-Eksel (BE)

(73) Assignee: Koninklijke Philips Electronics N.V., Eindhoven (NL)

( * ) Notice: Subject to any disclaimer, the term of this patent is extended or adjusted under 35 U.S.C. 154(b) by 77 days.

(21) Appl. No.: 12/526,567

(22) PCT Filed: Feb. 13, 2008

(86) PCT No.: PCT/IB2008/050512
§ 371 (c)(1),
(2), (4) Date: Feb. 19, 2010

(87) PCT Pub. No.: WO2008/099346
PCT Pub. Date: Aug. 21, 2008

(65) Prior Publication Data
US 2010/0140146 A1 Jun. 10, 2010

(30) Foreign Application Priority Data
Feb. 16, 2007 (EP) .................................. 07102553

(51) Int. Cl.
*B03C 1/00* (2006.01)

(52) U.S. Cl. ............ 209/214; 209/38; 209/39; 209/215; 209/227; 209/232

(58) Field of Classification Search .................. 209/38, 209/39, 214, 215, 223.1, 227, 232
See application file for complete search history.

(56) References Cited

U.S. PATENT DOCUMENTS

| | | | | |
|---|---|---|---|---|
| 3,289,836 A * | 12/1966 | Weston | ..................... | 209/214 |
| 4,668,383 A * | 5/1987 | Watson | ..................... | 209/216 |
| 5,466,574 A * | 11/1995 | Liberti et al. | .................... | 435/5 |
| 5,944,195 A * | 8/1999 | Huang et al. | .................... | 209/39 |
| 6,346,196 B1 | 2/2002 | Bose | | |
| 7,506,765 B2 * | 3/2009 | Franzreb et al. | .............. | 209/232 |
| 7,681,737 B2 * | 3/2010 | Armstrong et al. | ........... | 209/225 |
| 2002/0134730 A1 | 9/2002 | Bose | | |

FOREIGN PATENT DOCUMENTS

| | | |
|---|---|---|
| CN | 1772390 | 5/2006 |
| DE | 10151778 A1 | 5/2003 |
| EP | 1304542 A2 | 4/2003 |
| WO | 2004078316 A1 | 9/2004 |
| WO | 2006136237 A1 | 12/2006 |

* cited by examiner

*Primary Examiner* — Terrell Matthews (57) ABSTRACT

Magnetic Particle Imaging (MPI) requires high-performing tracer materials that are highly magnetic monodispersed particles with fast remagnetization behavior. Known separation techniques only allow for fractionation of magnetic particles based on differences in magnetic volume. Proposed is a separation method, which allows for separation of magnetic particles with respect to their dynamic response onto an oscillating high gradient magnetic field.

23 Claims, 6 Drawing Sheets

METHOD AND SEPARATOR SYSTEM FOR SEPARATING MAGNETIC PARTICLES, SEPARATOR COLUMN FOR USE IN A SEPARATOR SYSTEM

The present invention relates to a method for separating magnetic particles. Furthermore, the invention relates to a separator system for separating magnetic particles and to a separator column for use in a separator system.

A method of magnetic particle imaging is known from German Patent Application DE 101 51 778 A1. In the case of the method described in that publication, first of all a magnetic field having a spatial distribution of the magnetic field strength is generated such that a first sub-zone having a relatively low magnetic field strength and a second sub-zone having a relatively high magnetic field strength are formed in the examination zone. The position in space of the sub-zones in the examination zone is then shifted, so that the magnetization of the particles in the examination zone changes locally. Signals are recorded which are dependent on the magnetization in the examination zone, which magnetization has been influenced by the shift in the position in space of the sub-zones, and information concerning the spatial distribution of the magnetic particles in the examination zone is extracted from these signals, so that an image of the examination zone can be formed. Such an arrangement and such a method have the advantage that it can be used to examine arbitrary examination objects—e. g. human bodies—in a non-destructive manner and without causing any damage and with a high spatial resolution, both close to the surface and remote from the surface of the examination object.

The performance of the known method depends strongly on the performance of the tracer material, i.e. the material of the magnetic particles. There is always the need to increase the signal to noise ratio of known arrangements in order to improve the resolution and the application of such a method to further applications.

It is therefore an object of the present invention to provide a method such that improved magnetic particles result, especially for an application in magnetic particle imaging.

The above object is achieved by a method for separating magnetic particles, wherein the particles are circulated at least once through a separator column with a matrix, the method comprising:

a size selection step, wherein the particles are selected according to their size, and an AC fractionating step, wherein the particles in the separator column are subjected to an oscillating high gradient magnetic field.

The advantage of such a method is that it is possible to obtain magnetic particles having a comparably sharp distribution of both a size and thus a magnetic volume of the particles and their dynamic response to the oscillating high gradient magnetic field which depends inter alia upon their strength of anisotropy of their magnetization. Obtained particles advantageously increase the signal to noise ratio when used in the context of magnetic particle imaging techniques. In the context of the present invention, the term "strength of anisotropy of the magnetization of magnetic particles" signifies the exterior magnetic field (exterior relative to the magnetic particle or particles) that is necessary in order to change significantly the magnetization of the magnetic particle or particles. This interpretation is strongly correlated to other definitions relatable to the term "anisotropy of magnetic particles" or "field of anisotropy", e.g. different energies related to different spatial directions (energy landscape) expressed by means of a plurality of constants of anisotropy. In the context of the present invention, the term "strength of anisotropy of the magnetization of magnetic particles" is related to a quantifiable parameter.

According to a preferred embodiment of the present invention, the size selection step is a DC fractionating step, wherein the particles are captured by the matrix, due to an attractive force between the particles and the matrix, a strength of the attractive force depending upon a strength of a magnetic moment of the particles. Preferably, the column is filled with (e.g. stainless steel) microgranules or another matrix material such a steel wool, wires, filaments or grids. It is subjected to the application of the constant external magnetic field so that high field gradients are created at the surface of the matrix. The magnetic particles are fed through the column and, when subjected to the constant magnetic field, the particles are magnetized in the direction of the constant magnetic field and attracted to the matrix. The "strength of the magnetic moment of the particle" in the sense of the invention relates to an induced magnetic dipole moment of the particle. The attractive magnetic force acting on the particles depends upon this induced magnetic dipole moment of the particle. With a given magnetic field gradient, particles with a certain strength of the magnetic moment of the particle which is also referred to as magnetic volume or magnetic size of the particle, are effectively captured. A reduction (e.g. step-like) of the external constant magnetic field results in the release of particles with a narrow size distribution.

According to another preferred embodiment of the present invention, the particles, in the AC fractionating step, are remagnetized by the oscillating high gradient magnetic field, and the particles are captured by the matrix, due to an attractive force between the particles and the matrix, a strength of the attractive force depending upon a remagnetization time of the particles. Particles with different magnetic anisotropy yield different remagnetization times which advantageously allows a discrimination of the particles depending upon their magnetic anisotropy. The threshold of the remagnetization time which is short enough for the particles to be captured, is advantageously settable by choosing an appropriate frequency of the oscillation of the oscillating high gradient magnetic field. A frequency of the oscillating magnetic field being preferably in a range from 1 kHz to 2 MHz, more preferably in a range from 10 kHz to 200 kHz. The magnetization of the particles with relatively short remagnetization times will be able to follow the oscillating high gradient magnetic field. In effect, those particles are captured by the matrix. The magnetization of particles with relatively long remagnetization times will lag behind and decrease in the oscillating high gradient magnetic field. As a result, the magnetic force between these particles and the matrix is significantly reduced and the particles are not captured, but circulated through the column.

According to a further preferred embodiment of the present invention, the size selection step, in particular a DC fractionating step, is started prior to the AC fractionating step. The discrimination of the particles according to their magnetic anisotropy is advantageously efficient from a substantially monodisperse set of particles regarding their magnetic moment. The person skilled in the art will recognize, that the DC fractionating step and the AC fractionating step may be executed separately, regarding time and place. Further, the DC fractionating step and the AC fractionating step, however, need not necessarily be subsequent, but may, at least partly, coincide. The constant high gradient magnetic field is preferably at least partially sustained, when the AC fractionating step is started. More preferable, the constant high gradient magnetic field is reduced during a transient time period and the AC fractionating step is started during the transient time period.

According to still a further preferred embodiment of the present invention, the method further comprises at least one release step, wherein the particles which are captured by the matrix are released from the column by circulating a fluid through the column, in particular in absence of any magnetic field, the release step following the DC fractionating step and/or the AC fractionating step.

According to still a further preferred embodiment of the present invention, the method further comprises a wash step prior to the release step, the column being flushed with a buffer solution in the wash step, in order to remove particles from the column which are not captured by the matrix.

According to still a further preferred embodiment of the present invention, the method further comprises a concentration step, wherein a concentration of the magnetic particles in a fluid is increased. The skilled artisan recognizes that the magnetic particles are dispersed in a certain amount of fluid, in particular in a gasile or liquid fluid. The multiple discrimination of the particles in the DC fractionating step and the AC fractionating step leaves behind a fluid with a low concentration of sharply distributed magnetic particles, in terms of their magnetic moment and their magnetic anisotropy. Advantageously, by a concentration step, a fluid is reached which can be measured using a newly designed magnetic particle spectrometer (MPS) and/or that can be detected by scanners used for magnetic particle imaging (MPI).

For concentration, different techniques can be utilized such as, for example, vacuum evaporation. In a preferred embodiment, the concentration step comprises repeatedly circulating the fluid through a separator column and subjecting the particles in the separator column to a magnetic field, a void volume of the separator column preferably being substantially smaller than a volume of the fluid. The person skilled in the art will recognise that the same column as for the DC fractionating step or the AC fractionating step might be used. However, a smaller column will advantageously provide a higher grade of concentration. In this embodiment of the concentration step, the separator column based high gradient magnetic separation (HGMS) is advantageously used to capture possibly all the highly discriminated particles in the matrix of the column, in order to reduce the amount of fluid. Furthermore preferred, the method comprises an agglomeration reversion step, wherein agglomerated particles are decollated, preferably by ultrasonic pulses.

A further advantage of the method according to the invention is, that it can be easily developed into an automated method and system.

The invention further relates to a separator system for separating magnetic particles by a method according to the present invention, the system comprising at least one separator column, a first magnet device for application of a constant high gradient magnetic field and a second magnet device for application of the oscillating high gradient magnetic field.

With the separator system according to the invention, it is advantageously possible to provide a simple and efficient separation of magnetic particles depending upon both a magnetic volume of the particles and the strength of anisotropy of their magnetization.

According to a preferred embodiment of the invention, the first magnet device comprises electromagnets which advantageously provide high flexibility. However, permanent magnets may be used as well. The second magnet device preferably comprises an electromagnet with one or more coils, operable with alternate current. Furthermore preferable, a vector of the constant high gradient magnetic field is parallel or perpendicular with respect to a vector of the oscillating high gradient magnetic field, the latter option advantageously allowing for a compact and efficient implementation of the separator system.

According to a further preferred embodiment of the invention, a magnetic field strength of the constant high gradient magnetic field is in the order of 1 mT (millitesla) to 100 mT and wherein a magnetic field strength of the oscillating high gradient magnetic field is in the order of 1 mT to 25 mT.

The person skilled in the art will recognise that, in order to obtain the particular magnetic field strength, the value specified as the magnetic field strength in tesla in the context of the present invention, in each case has to be divided by the magnetic field constant $\mu_0$, as tesla is the unit of the magnetic flux density.

The invention further relates to a separator column for use in a separator system, in particular a separator system according to the invention, the separator column comprising a tube and a matrix, the matrix being adapted to capture at least one component of a mixture of magnetic particles as the mixture is circulated through the tube, wherein the matrix comprises a soft magnetic material. A tube in the sense of the present invention is any structure which allows a fluid flow through it, independent of its cross sectional form. Generally, the cross section of a column tube will be circular, however, any angular or elliptic shapes may as well be applied within the scope of the invention.

Regarding the use of a preferably medium frequency oscillating high gradient magnetic fields for obtaining magnetic particles according to the method as described in here before, existing separator columns comprise a disadvantage, due to heating effects caused by hysteretic losses in the matrix, for example ferromagnetic granules. A matrix of soft magnetic material is advantageously less susceptible to heating losses. Preferably, the soft magnetic material is a soft ferrite.

According to a preferred embodiment of the invention, the soft magnetic material comprises granules which are coated with a coating, the coating providing a relative positioning of the granules with respect to one another. More preferable, the coating comprises a lacquer. The soft magnetic granules preferably have a diameter or size of at least 100 μm, more preferably greater than about 200 μm and less than about 2000 μm, still more preferably greater than about 200 μm and less than about 1000 μm, and most preferably about 280 μm. The separator column or the separator system preferably comprises at least one pump for circulating the fluid through the column, preferably at a flow rate of about 1 ml per minute. The use of a pump advantageously allows an automation of the separator system according to this embodiment of the invention.

According to a further preferred embodiment of the invention, the tube is made of a heat resistant material, such as, for example, glass. Still further preferred the separator column comprises a cooling device for cooling the tube, in particular an air-cooling or water-cooling. This advantageously increases the temperature range in which the separator column may be utilized. Thus, also ferromagnetic material, in particular soft ferromagnetic material may be used as matrix material.

These and other characteristics, features and advantages of the present invention will become apparent from the following detailed description, taken in conjunction with the accompanying drawings, which illustrate, by way of example, the principles of the invention. The description is given for the sake of example only, without limiting the scope of the invention. The reference figures quoted below refer to the attached drawings.

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes.

Where an indefinite or definite article is used when referring to a singular noun, e.g. "a", "an", "the", this includes a plural of that noun unless something else is specifically stated.

Furthermore, the terms first, second, third and the like in the description and in the claims are used for distinguishing between similar elements and not necessarily for describing a sequential or chronological order. It is to be understood that the terms so used are interchangeable under appropriate circumstances and that the embodiments of the invention described herein are capable of operation in other sequences than described of illustrated herein.

Moreover, the terms top, bottom, over, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the present description and claims, should not be interpreted as being restricted to the means listed thereafter; it does not exclude other elements or steps. Thus, the scope of the expression "a device comprising means A and B" should not be limited to devices consisting only of components A and B. It means that with respect to the present invention, the only relevant components of the device are A and B.

Figure 1A:
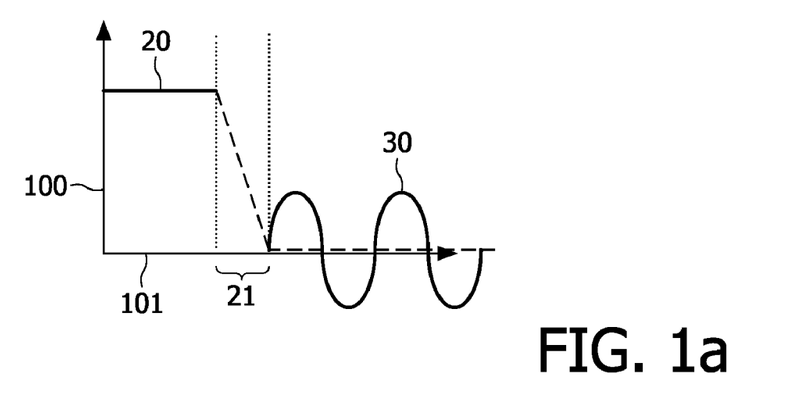
FIGS. 1a, 1b and 1c illustrate schematically chronological sequences of the method in diagrams, according to the present invention.
Figure 1B:
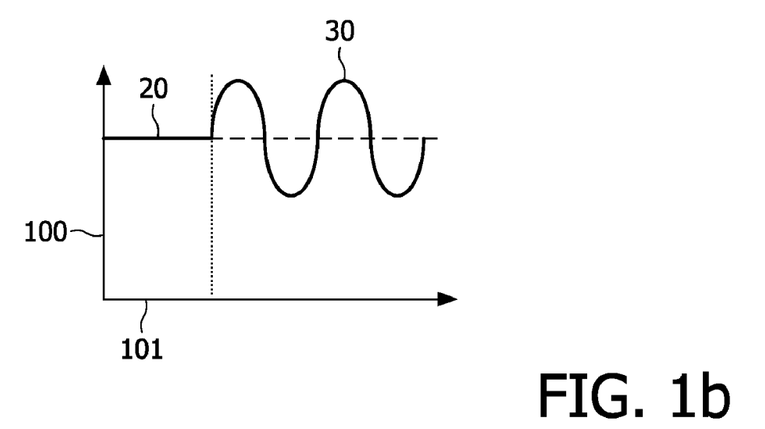
Figure 1C:
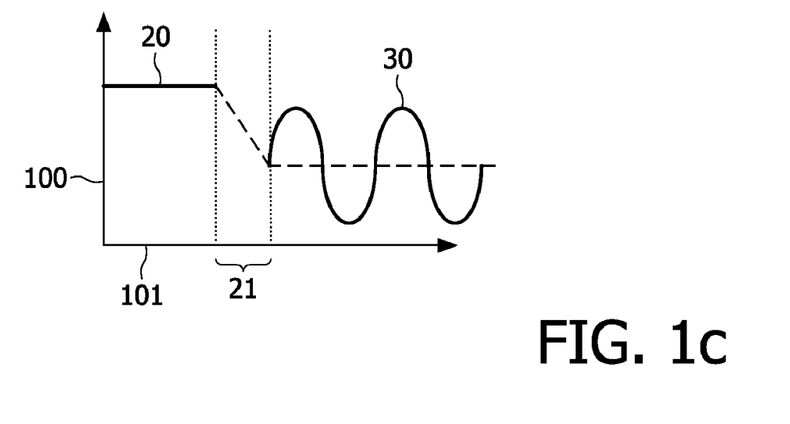

FIGS. 1a, 1b and 1c show chronological sequences (axis of abscissae 101) of the magnetic field strength on the axis of ordinates 100. As a size selection step, a DC fractionating step is depicted. The person skilled in the art will recognise that other size selective methods for the size selection step are known in the art, such as, for example, field flow fractionation (FFF), centrifugation or mechanical filtration. In the DC fractionating step, particles (FIG. 3) in a separator column (FIG. 2a) are subjected to a constant high gradient magnetic field 20. In the sequence of FIG. 1a the strength of the high gradient magnetic field 20 is reduced to zero over a transient time period 21, whereas in FIG. 1c the high gradient magnetic field 20 is reduced to a level above zero over the transient time period 21. In the AC fractionating step, an oscillating high gradient magnetic field 30 is applied, which may either interfere with the high gradient magnetic field 20 (FIG. 1b) or with the sustaining magnetic field after reduction (FIG. 1c), or which replaces the high gradient magnetic field 20 (FIG. 1a). Although not shown, the application of the oscillating high gradient magnetic field 30 may as well start during the transient time period 21.

Figure 2A:
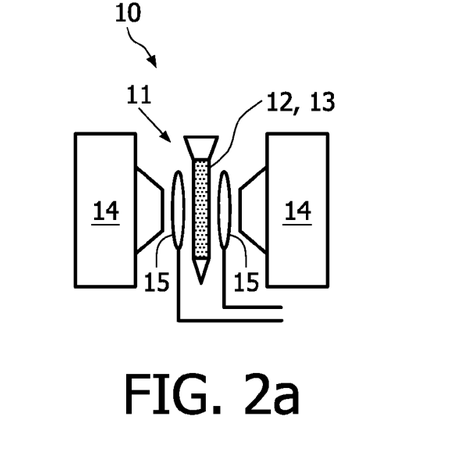
FIGS. 2a, 2b, 2c and 2d illustrate schematically implementations of the separator system, according to the present invention.
Figure 2B:
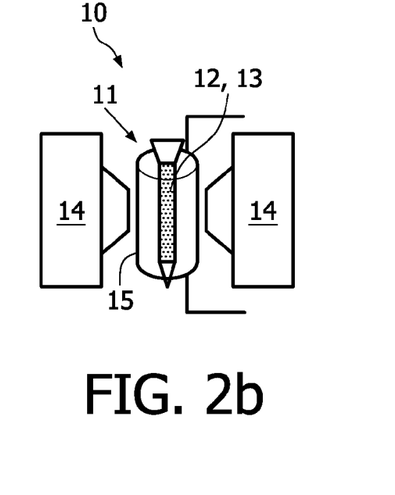
Figure 2C:
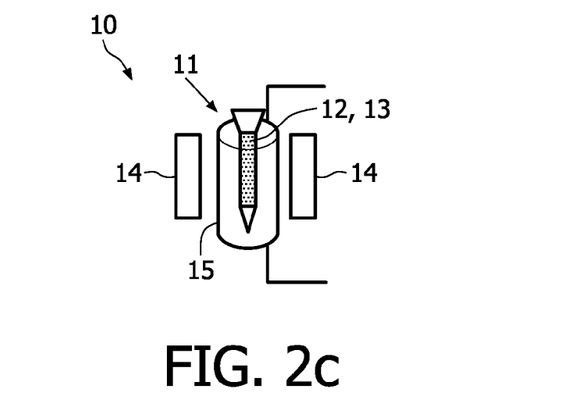
Figure 2D:
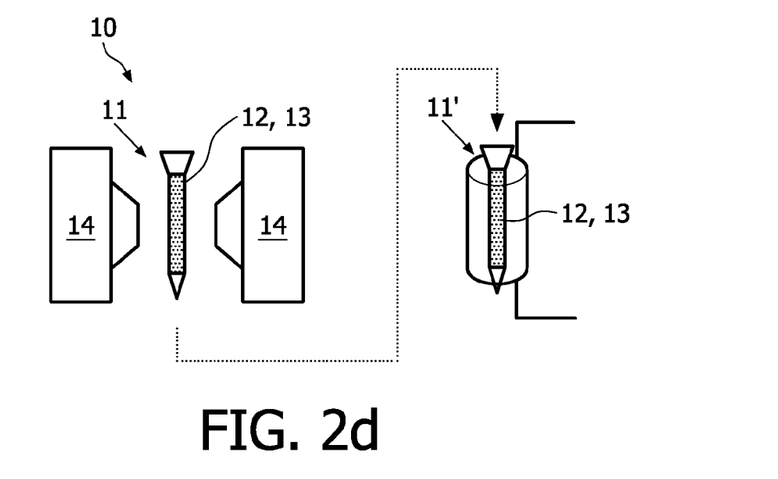

In FIGS. 2a, 2b, 2c and 2d implementations of a separator system 10 according to the invention are depicted. The system 10 comprises a separator column 11, a first magnet device 14 for application of the high gradient magnetic field, and a second magnet device 15 for application of the oscillating high gradient magnetic field. The separator column 11 comprises a tube 13, partly filled with a matrix 12, which will be described in more detail in conjunction with FIG. 6. In FIGS. 2a and 2b, the first magnet device 14 comprises electromagnets which are advantageously flexible in use. However, permanent magnets may be used as well for the first magnet device, as shown in FIG. 2c. In FIG. 2a, the oscillating high gradient magnetic field is applied by a second magnet device 15 with two electromagnet coils. The oscillating high gradient magnetic field and the high gradient magnetic field are directed in the same direction, in this case. As shown in FIGS. 2b and 2c, the direction of the oscillating high gradient magnetic may as well be perpendicular to the high gradient magnetic field. The second magnet device 15 thus comprises a single electromagnet coil around the column 11, which allows for an advantageously compact buildup of the separator system 10. In FIG. 2d, the separator system is split into two parts. In the left hand part, the DC fractionation step in a column 11 is depicted, whereas the AC fractionating step in a column 11' is depicted on the right hand side. The dotted line illustrates, that the method steps of the method according to the invention may be executed at different times and places.

Figure 3:
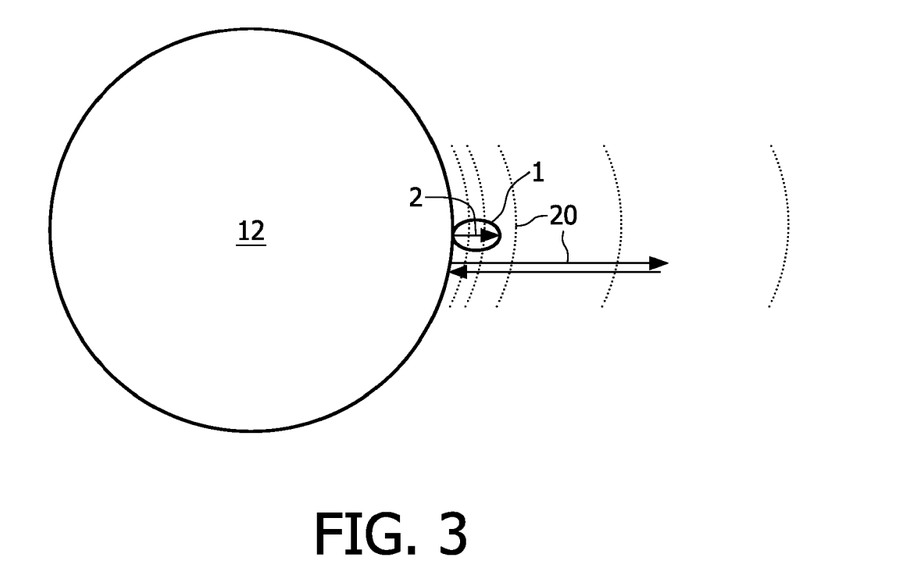
FIG. 3 illustrates schematically the DC fractionating step, according to the present invention.

FIG. 3 illustrates an operation principle of a high gradient magnetic separator (HGMS) which is applied in the DC fractionating step according to the present invention. A separator column (not shown) filled with a matrix material 12 such a steel wool, wires, filaments or grids, is subject to the application of the external magnetic field 20 (depicted by bi-directional arrows and streamlines of the field) so that high field gradients are created at the surface of a matrix microgranule 12. If a solution of magnetic particles 1 is fed through the separator column, placed in a constant magnetic field 20, the particles 1 are magnetized in the direction of the constant magnetic field 20 and attracted to the microgranules 12. The attractive magnetic force acting on the particle 1 depends on an induced magnetic dipole moment (depicted by arrow 2) of the particle and on the magnetic field gradient. Due to the high magnetic gradients, the particles 1 with a certain magnetic volume are captured. A competition of hydrodynamic forces and magnetic forces establishes a build-up of particles 1 of a certain magnetic size. A preferably stepwise reduction of the external magnetic field 20 results in the release of particles 1 with a narrow size distribution. This method step provides fractionation by magnetic volume.

Figure 4:
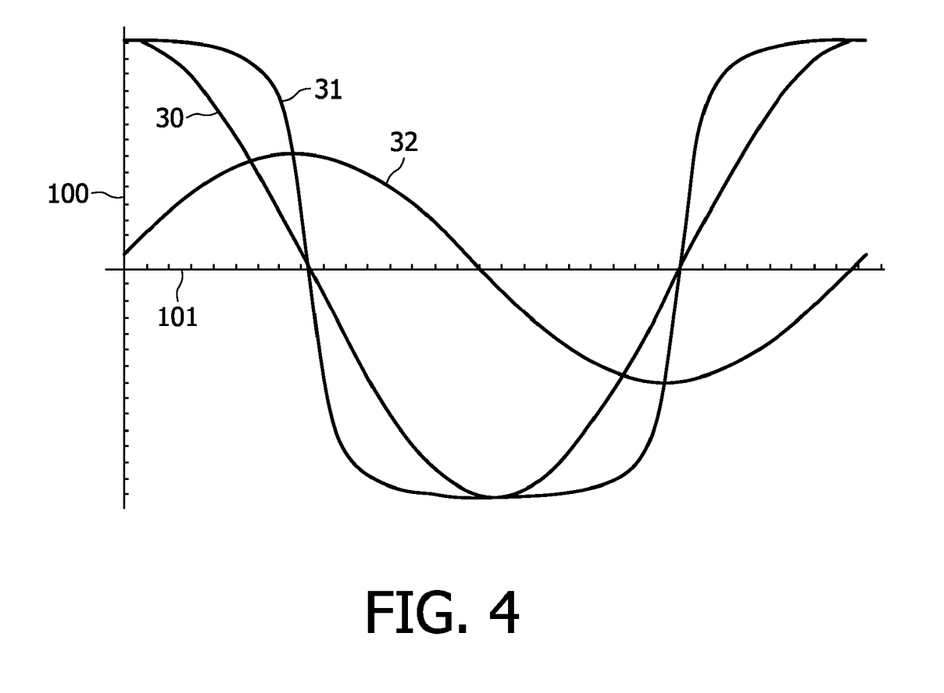
FIG. 4 illustrates the AC fractionating step, according to the present invention, in a diagram.

In the AC fractionating step, magnetic anisotropy properties of the particles 1 are probed. In FIG. 4, the effect of the oscillating high gradient magnetic field 30 is schematically illustrated. Again, magnetic field strength or magnetization strength is depicted on the axis of ordinates 100, and the axis of abscissae 101 shows the time. Line 31 shows the magnetization of a so-called relatively 'fast' particle (low magnetic anisotropy), which is able to follow the externally applied oscillating high gradient magnetic field 30. As a result, the magnetic force between the particle 1 and the matrix 12 (FIG.

3) will remain attractive during the AC fractionating step, or in other words, the 'fast' particles are captured. It is to be noted that also in this case, magnetic attraction competes with flow based and Brownian particle motion. However, the overall effect results in magnetic attraction in the separator column. For 'slow' particles (line 32), however, due to a time delay in the particle's response to the oscillating high gradient magnetic field 30 (combination of high anisotropy and size), the magnetization 32 has a reduced magnitude and is phase-shifted with respect to the applied oscillating high gradient magnetic field 30. The attractive magnetic force is thus reduced, due to the reduction in magnitude of the magnetic particle. As a result, the effect of particle capture is strongly reduced and the particle is circulated out of the separator column (not depicted). It is to be noted that the forces (flow based and Brownian particle motion) are the same for 'fast' and 'slow' particles, provided they have been separated on size before. The skilled artisan will recognise that the frequency of oscillation of the oscillating high gradient magnetic field defines the threshold between slow and fast magnetizable particles.

Figure 5:
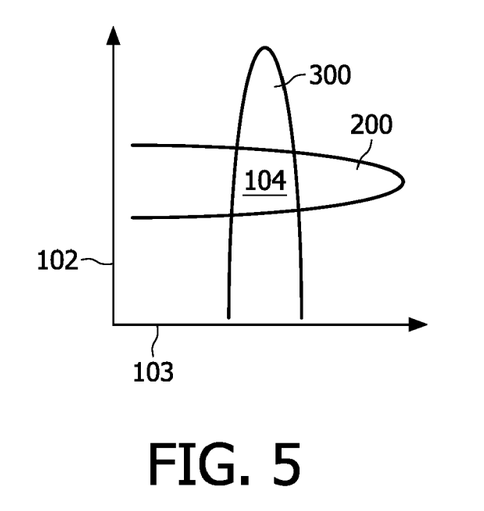
FIG. 5 illustrates the selection of particles, according to the present invention.

In FIG. 5, the selection of particles, according to the present invention is illustrated. It is anticipated that, in a particular particle assay, there is a relationship between magnetic anisotropy and magnetic moment. In a mixture of poly-grain ironoxide particles, e.g. Resovist, particle magnetic anisotropy will be set by a combination of shape and intrinsic anisotropy. Shape anisotropy is a strong function of the ellipticity of the particles. The intrinsic anisotropy direction is distributed over the collection of grains within the particle. On the axis of ordinates 102 the magnetic anisotropy of the particles is depicted. On the axis of abscissae 103, the magnetic moment of the particles is depicted. In the DC fractionating step the particles are discriminated with regard to their magnetic moment and the particles under curve 300 are selected. In the AC fractionating step, the particles are discriminated regarding their anisotropy, so that, for example, particles covered by curve 200 are captured. The combination of both steps provides an intersection 104 of particles which are discriminated according to their magnetic anisotropy and their magnetic moment. The person skilled in the art recognises that a certain sequence of the method steps is not necessarily needed.

Figure 6:
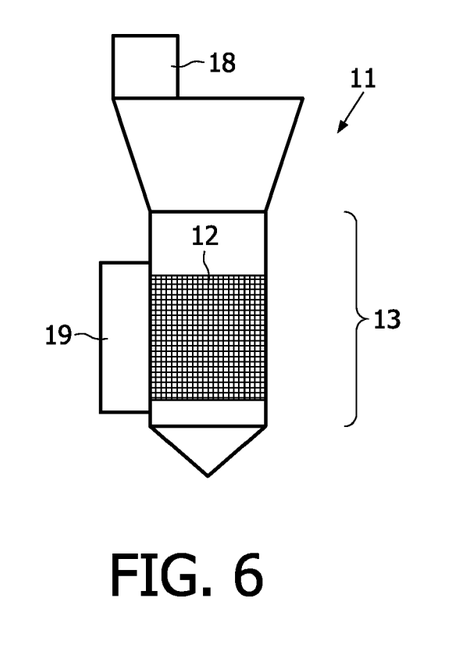
FIG. 6 illustrates schematically a separator column, according to the present invention.

In FIG. 6 a separator column 11 according to the invention is schematically illustrated. The tube 13 is at least partly filled with a matrix 12 of soft magnetic material, in particular of a soft ferrite which reduces hysteretical losses and thus prevents heating of the separator column 11. Experimentally, it has been found that the use of an oscillating high gradient magnetic field of 25 kHz with increasing amplitude leads to unacceptable temperature rise in the separator column 11. An oscillating high gradient magnetic field of 10 mT can be sustained for up to one hour, whereas a 25 mT magnetic field amplitude results in immediate strong heating effect. The key aspect is the reduction of hysteretic losses in the matrix 12. Therefore, the soft magnetic material that is being used, preferably exhibits a closed (S-like) magnetization curve (hysteresis loop). Alternatively and/or additionally preferred, the tube 13 is made of a heat resistant material, such as glass, to improve the temperature range in which the column 11 can be utilized, the use of coating materials for the matrix 12, again to sustain a wider temperature range, or the use of direct or indirect cooling 19, by air or liquid. A pump 18 pumps the fluid through the column 11.

Figure 7A:
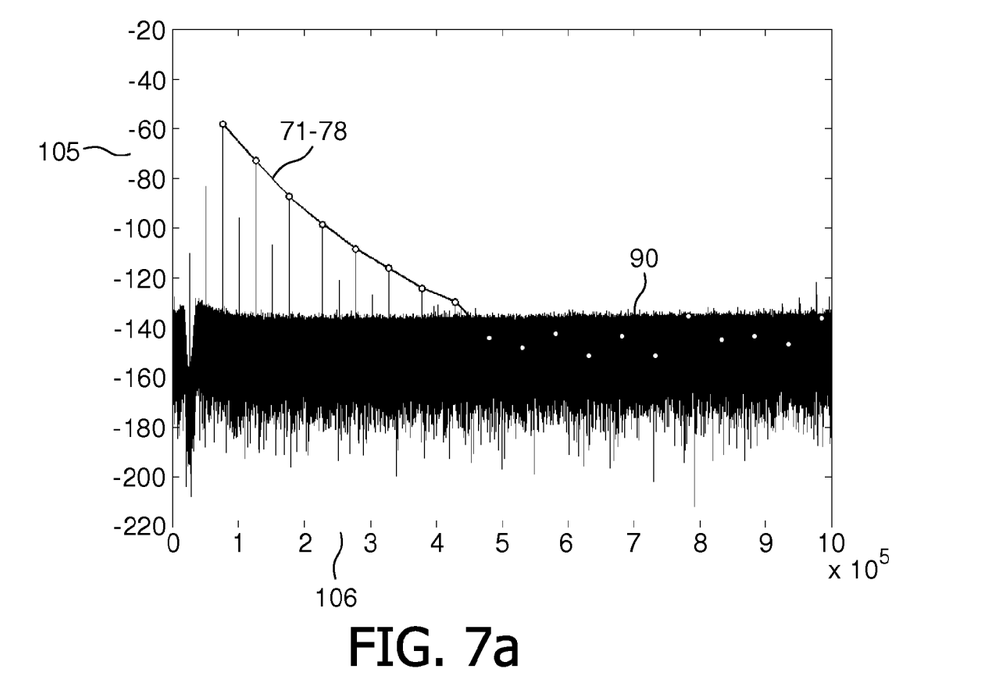
FIGS. 7a, 7b and 7c illustrate a detectable signal strength of magnetic particles separated according to the present invention, compared to unseparated magnetic particles.
Figure 7B:
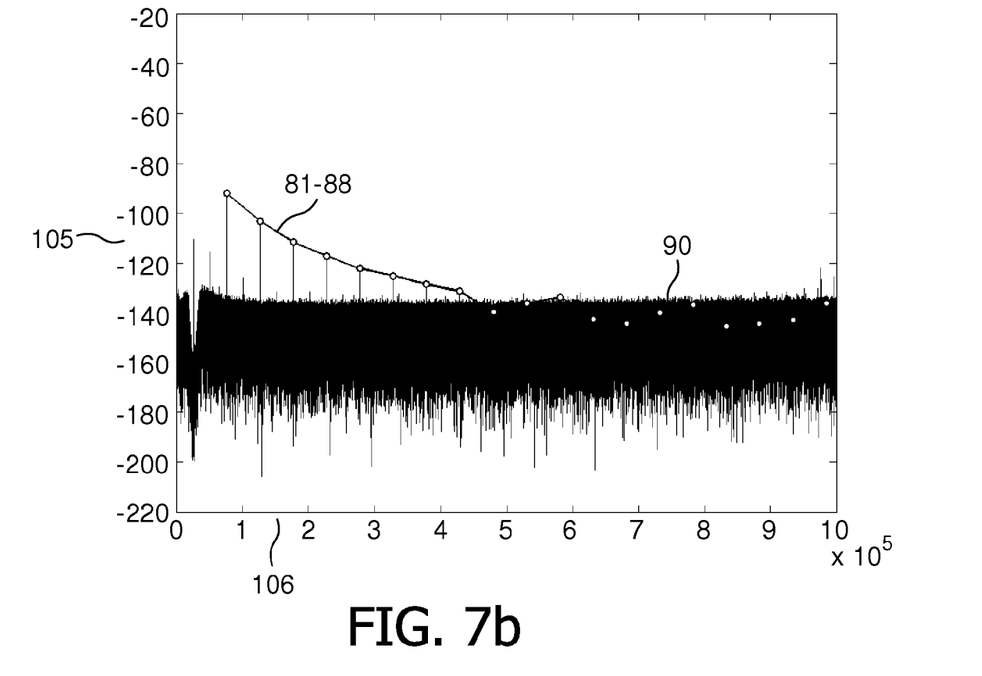
Figure 7C:
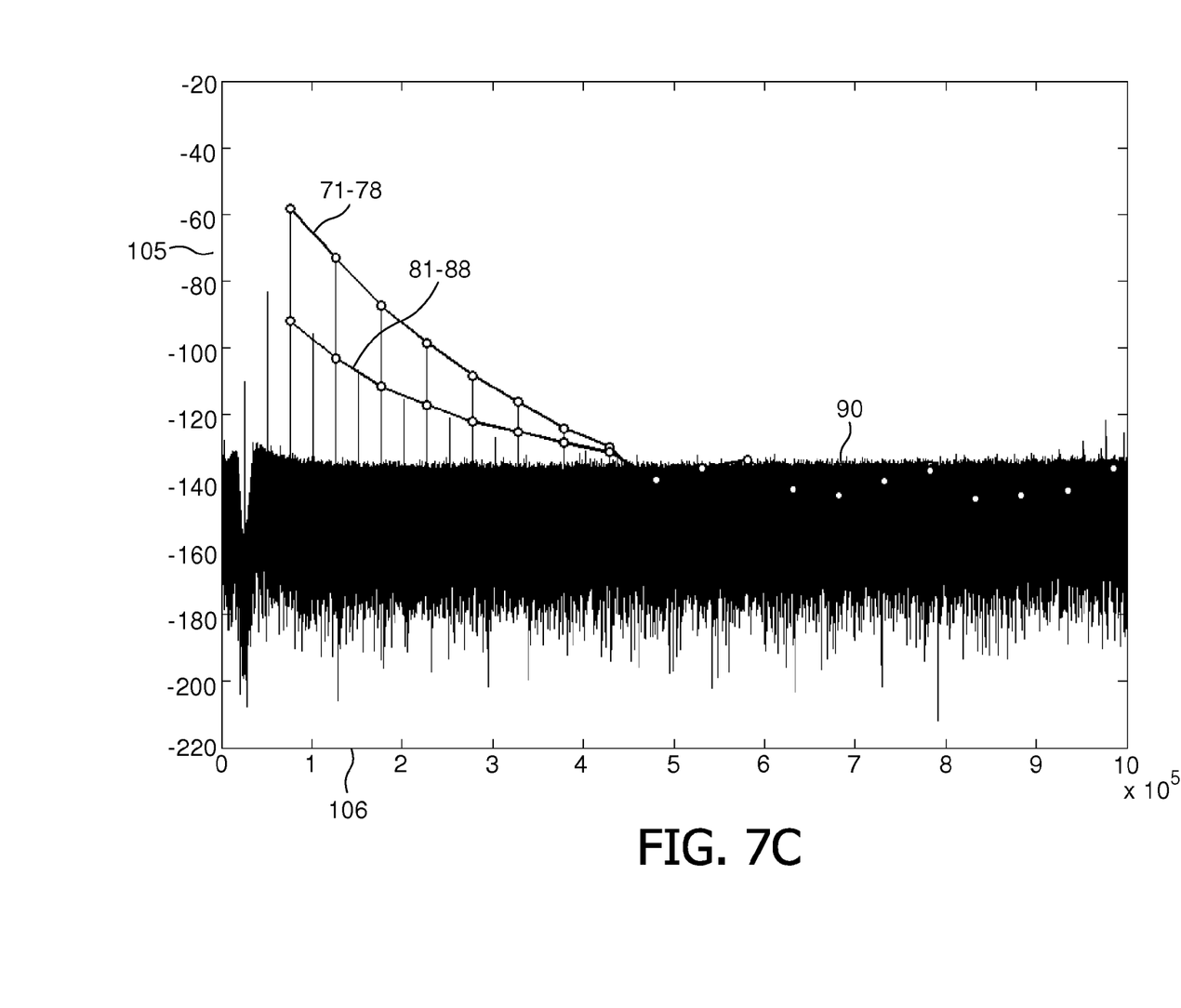

FIGS. 7a, 7b and 7c illustrate a detectable signal strength of magnetic particles separated according to the present invention, compared to unseparated magnetic particles. On the axis of ordinates 105 a signal strength of a measurement with a magnetic particle spectrometer is shown and on the axis of abscissae 106 a frequency is shown. The points 71 to 78 and 81 to 88 show harmonics of the first (71, 81) to eighth order of magnetic particle spectrometer measurement of a particle assay before (FIG. 7a) and after the AC fractionating step (FIG. 7b). It is important in magnetic particle imaging that the signal strength in particular of the higher harmonics is well above the noise level 90. In FIG. 7c, both measurement results are depicted in one diagram. The signal strength of the particle assay after the AC fractionating step is generally lower than the signal strength of the starting particle assay. As can be determined from the signal of the first harmonic, this is because of the overall reduction in the number of particles. The particle assay after the AC fractionating step comprises only about one sevenhundredth of the particles in the starting particle assay. So, if the particle assay after the AC fractionating step had the same particle concentration, the signals of the first harmonics 71, 81 would have the same strength and thus the signal of the third and higher harmonics (83 to 88) of the particle assay after the AC fractionating step would be stronger than those of the starting particle assay (73 to 78), because the slope of the curve 81 to 88 is less steep than the slope of the curve 71 to 78.

The invention claimed is:

1. A method for separating magnetic particles, wherein the particles are circulated at least once through at least one separator column with a matrix, the method comprising the acts of: performing a size selection act differentiating the particles using, an attractive force between the particles and the matrix, a strength of attractive force depending upon a strength of a magnetic moment of the particles wherein the particles are selected according to their size, performing an AC fractionating act differentiating the particles using a strength of anisotropy of their magnetization, wherein the particles in the separator column are subjected to a high gradient oscillating magnetic field, wherein the size selection act, is started prior to the AC fractioning act.

2. The method according to claim 1, wherein the size selection act is a DC fractioning act, wherein the particles in the separator column are subjected to a constant high gradient magnetic field, the particles being captured by the matrix during the DC fractioning act due to the attractive force.

3. The method according to claim 1, wherein the particles in the AC fractionating act are remagnetized by the oscillating high gradient magnetic field, and wherein the particles are captured by the matrix, due to the attractive force between the particles and the matrix, a strength of the attractive force depending upon a remagnetization time of the particles, a frequency of the oscillating high gradient magnetic field being in a range from 1 kHz to 2 MHz.

4. The method according to claim 1, further comprising performing at least one release act, wherein the particles which are captured by the matrix are released from the column by circulating a fluid through the column in absence of any magnetic field, the release act following at least one of the AC fractionating act and a DC fractionating act.

5. The method according to claim 4, further comprising performing a wash act prior to the release act, the column being flushed with a buffer solution during the wash act to remove particles from the column which are not captured by the matrix.

6. The method according to claim 1, wherein the size selection act is a DC fractionating act.

7. The method according to claim 2, wherein at least one of the constant high gradient magnetic field is at least partially sustained, when the AC fractionating act is started, and the constant high gradient magnetic field is reduced during a transient time period and the AC fractionating act is started during the transient time period.

8. The method according to claim 1, further comprising performing a concentration act, wherein a concentration of separated particles in a fluid is increased.

9. The method according to claim 8, the concentration act comprising acts of repeatedly circulating the fluid through a separator column and subjecting the particles in the separator column to a magnetic field, a void volume of the separator column preferably being substantially smaller than a volume of the fluid.

10. The method according to claim 8, further comprising an act of performing an agglomeration reversion act, wherein agglomerated particles are decollated by ultrasonic pulses.

11. A separator system for separating magnetic particles, the system comprising: at least one separator column; a first magnetic device configured to apply a constant high gradient magnetic field during size selection differentiating the particles using an attractive force between the particles and the matrix, a strength of the attractive force depending upon a strength of a magnetic moment of the particles, wherein the particles are selected according to size; and a second magnet device configured to apply AC fractionating differentiating the particles using a strength of anisotropy of their magnetization, wherein the particles on the separator column are subjected to an oscillating high gradient magnetic field, wherein the particles are circulated at least once through the separator column, and wherein the size selection is started prior to the AC fractionating.

12. The separator system according to claim 11, wherein the first magnet device comprises electromagnets or permanent magnets.

13. The separator system according to claim 11, wherein the second magnet device comprises an electromagnet with one or more coils, operable with alternate current.

14. The separator system according to claim 11, wherein a vector of the constant high gradient magnetic field is parallel or perpendicular with respect to a vector of the oscillating high gradient magnetic field.

15. The separator system according to claim 11, wherein a field strength of the constant high gradient magnetic field is in the order of 1 mT to 100 mT and wherein a field strength of the oscillating high gradient magnetic field is in the order of 1 mT to 25 mT.

16. A separator column for separating magnetic particles circulated there through, the separator column comprising: a tube; a matrix adapted to capture at least one component of a mixture of the magnetic particles as the mixture is circulated through the tube, wherein the matrix comprises a soft magnetic material; a first magnet device configured to apply a constant high gradient magnetic field during size selection wherein the particles are selected according to size, the particles being differentiated using an attractive force between the particles and the matrix, a strength of the attractive force depending upon a strength of a magnetic moment of the particles; and a second magnet device configured to apply AC fractioning wherein the particles in the separator column are subjected to an oscillating high gradient magnetic field differentiating the particles using a strength of anisotropy of their magnetization wherein the size selection is started prior to the AC fractionating.

17. The separator column according to claim 16, wherein the soft magnetic material is a soft ferrite.

18. The separator column according to claim 16, wherein the soft magnetic material comprises granules which are coated with a coating, the coating providing a relative positioning of the granules with respect to one another.

19. The separator column according to claim 18, wherein the coating comprises a lacquer.

20. The separator column according to claim 16, wherein the tube is made of glass.

21. The separator column according to claim 16, further comprising a cooling device configured to cool the tube.

22. A method for separating magnetic particles, wherein the particles are circulated at least one through at least one separator column with a matrix, the method comprising acts of: performing a size selection act differentiating the particles using an attractive force between the particles and the matrix, a strength of the attractive force depending upon a strength of a magnetic moment of the particles, wherein the particles are selected according to their size; performing an AC fractionating act differentiating the particles using a strength of anisotropy of their magnetization, wherein the particles in the separator column are subjected to a high gradient oscillating magnetic field; and performing a concentration act, wherein a concentration of separated particles in a fluid is increased, the concentration act comprising repeatedly circulating the fluid through a separator column and subjecting the particles in the separator column to a magnetic field, a void volume of the separator column preferably being substantially smaller than a volume of the fluid.

23. A method for separating magnetic particles, wherein the particles are circulated at least once through at least one separator column with a matrix, the method comprising the acts of: performing a size selection act differentiating the particles using an attractive force between the particles and the matrix, a strength of the attractive force depending upon a strength of a magnetic moment of the particles, wherein the particles are selected according to their size; performing an AC fractioning act differentiating the particle using a strength of anisotropy of their magnetization, wherein the particles in the separator column are subjected to a high gradient oscillating magnetic field; and performing an agglomeration reversion act, wherein agglomerated particles are decollated by ultrasonic pulses.

* * * * *